United States Patent [19]
Mathys

[11] Patent Number: 4,840,631
[45] Date of Patent: Jun. 20, 1989

[54] ARTIFICIAL HIP JOINT SOCKET WITH HYDRAULIC HEAD SUPPORT

[75] Inventor: Robert Mathys, Bettlach, Switzerland

[73] Assignee: Robert Mathys Co., Bettlach, Switzerland

[21] Appl. No.: 162,249

[22] Filed: Feb. 29, 1988

Related U.S. Application Data

[63] Continuation-in-part of Ser. No. 864,727, filed as PCT CH85/00108 on Jul. 8, 1985, published as WO86/01394 on Mar. 13, 1986, abandoned.

[30] Foreign Application Priority Data

Aug. 28, 1984 [CH] Switzerland .................. 04121/84

[51] Int. Cl.$^4$ .............................................. A61F 2/32
[52] U.S. Cl. ................................................ 623/22
[58] Field of Search .................... 623/22, 23, 16, 18

[56] References Cited

U.S. PATENT DOCUMENTS

| | | | |
|---|---|---|---|
| 3,864,758 | 2/1975 | Yakich | 623/22 |
| 4,031,570 | 6/1977 | Frey | 623/22 |
| 4,676,799 | 6/1987 | Legrand | 623/22 |

FOREIGN PATENT DOCUMENTS

| | | | |
|---|---|---|---|
| 2229812 | 1/1974 | Fed. Rep. of Germany | 623/22 |
| 2742464 | 3/1979 | Fed. Rep. of Germany | 623/22 |
| 2060179 | 6/1971 | France | 623/22 |
| 2537868 | 6/1984 | France | 623/22 |
| WO86/01394 | 3/1986 | PCT Int'l Appl. | 623/22 |

*Primary Examiner*—Ronald L. Frinks
*Attorney, Agent, or Firm*—Walter C. Farley

[57] ABSTRACT

A liquid chamber (3) arranged in the bottom of the socket cavity (2) is latitudinally sealed by the engaging ball head (4) of the femoral prosthesis shaft. The ball head (4) of the hip joint prosthesis is supported hydrostatically by the liquid chamber (3) filled with synovia and sealed by the ball head following a deformation of the elastic sealing edge (5). By means of the hydrostatic support, the friction moment increases only a little when the load becomes higher and approaches a constant value which is considerably lower than in conventional hip joint sockets.

11 Claims, 1 Drawing Sheet

ARTIFICIAL HIP JOINT SOCKET WITH HYDRAULIC HEAD SUPPORT

This is a continuation-in-part of application Ser. No. 864,727, filed as PCT CH85/00108 on Jul. 8, 1985, published as WO86/01394 on Mar. 13, 1986, now abandoned.

BACKGROUND OF THE INVENTION

This invention relates to an artificial hip joint socket having the form of a hollow spherical segment.

The hitherto known artificial hip joint sockets manufactured predominantly from HDPE (High Density Polyethylene) exhibit with increasing load a linear increase of the friction moment between socket and ball head of the femoral prosthesis. Since peak loads as high as seven to eight times the amount of the body weight may occur with normal gait, conventional sockets exhibit considerable friction moments which may lead to excessive wear and loosening of the polyethylene cup.

SUMMARY OF THE INVENTION

An object of the present invention is to provide an artificial hip joint socket exhibiting only a minimal increase of the friction moment with rising load and possessing thereby optimal tribological properties.

According to the invention this is accomplished by providing a socket comprising a liquid chamber arranged in the bottom of the socket cavity which is latitudinally sealed by the engaging ball head of the artificial femoral shaft.

Due to this new design of the artificial hip joint socket according to the invention, hydrostatic support of the ball head of the femoral prosthesis is achieved in the liquid chamber filled with synovia and sealed by the deforming action of the ball head on an elastic sealing edge. With rising load, the friction moment increases only slightly and approaches a constant value which is significantly lower than with conventional hip joint sockets. In a hip joint according to the invention consisting of an elastic material, the liquid chamber is formed by a cavity in the spherical bottom of the socket, such that the transition zone between the spherical inner surface and the cavity is formed by the elastic sealing edge.

The artificial hip joint socket according to the invention may also be made of a hard material, e.g., metal or ceramics, with an elastic insert in the bottom of the socket designed as a liquid chamber with an elastic sealing edge. The insert may also have a sealing ring of elastic material. Preferably the liquid chamber is not arranged centrically at the bottom of the socket, but eccentrically so that it is positioned at the actual stress zone of the femoral ball head support under load. The diameter of the liquid chamber at its latitudinal sealing zone is dependent upon the other parameters of the artificial hip joint, but forms advantageously an aperture angle from 10° to 120°, preferably between about 30° and 90°, with respect to the center of the hollow sphere.

BRIEF DESCRIPTION OF THE DRAWINGS

The previously mentioned embodiments of the invention and some practical examples thereof are illustrated hereinafter by means of the drawings wherein.

DESCRIPTION OF THE PREFERRED EMBODIMENTS

Figure 1:
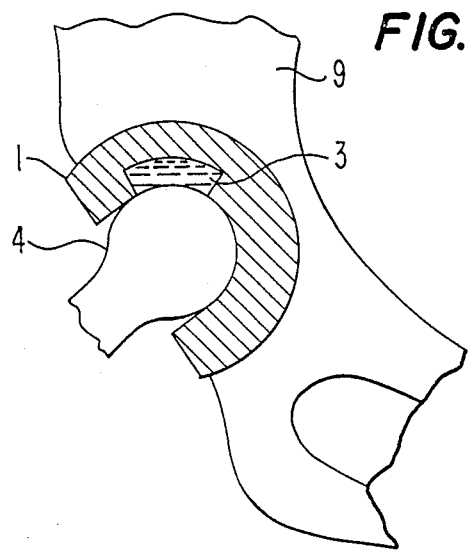
FIG. 1 shows an embodiment of the new hip joint socket in a section through the pelvis.

The hip joint socket 1, which may be made of one of the usual implant materials, has the form of a hollow spherical segment having a spherical inner surface 6 and comprises a liquid chamber 3 arranged in the bottom of the socket cavity 2. Socket 1 is implanted, as by known techniques, in pelvis 9 of a patient.

As can be seen from FIG. 1 the liquid chamber 3 is latitudinally (i.e., along a zone of the spherical inner surface 6) sealed by the engaging ball head 4 of the femoral prosthesis shaft. As seen in FIG. 1, the ball head 4 and spherical inner surface 6 have a common center about which the ball can rotate. Between ball head 4 and surface 6 is a layer of synovial fluid which can be displaced under loading conditions as indicated above.

Figure 2:
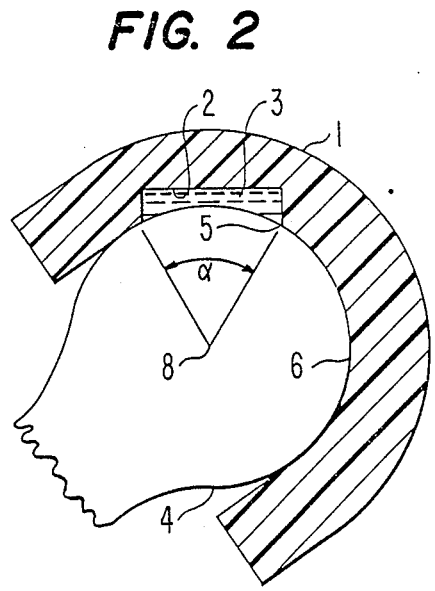
FIG. 2 shows a section in enlarged representation of an embodiment of the new hip joint socket made from an elastic material.

FIG. 2 shows an embodiment of the hip joint socket 1 made from an elastic, plastic material, e.g., from polyethylene (High Density Polyethylene (HDPE)), wherein the edge of the liquid chamber 3, i.e., the transition zone between spherical inner surface 6 and liquid chamber 3, is designed to have an elastic sealing edge 5. Upon loading of the artificial hip joint, the elastic sealing edge 5 deforms to a spherical shape which seals the liquid chamber 3 filled with synovia.

Figure 4:
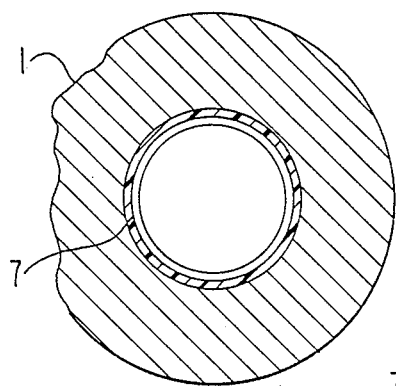
FIG. 4 is a transverse sectional view along line 4—4 of FIG. 3.
Figure 3:
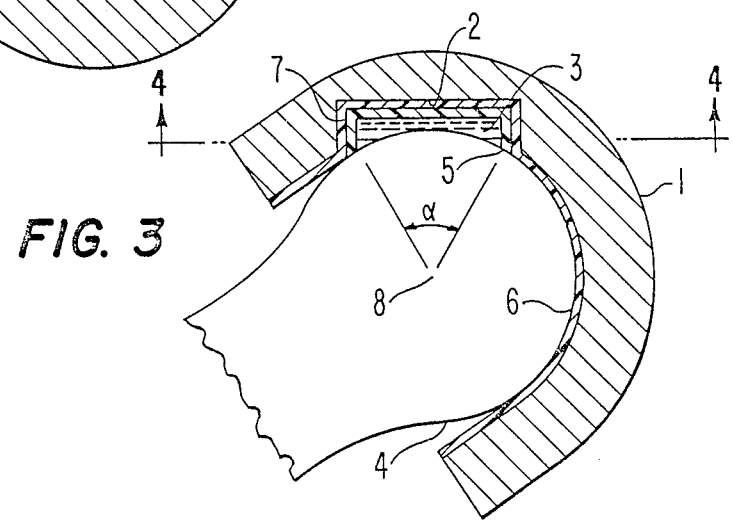
FIG. 3 shows a section in enlarged representation of an embodiment of the new hip joint socket made from a rigid material.

FIG. 3 shows an embodiment of the hip joint socket 1 made from a rigid material, e.g., from aluminum oxide ceramic. The sealing of the liquid chamber 3 is accomplished in this embodiment by means of an elastic insert 7 in the rigid socket cavity 2. As best seen in conjunction with the sectional view of FIG. 4, insert 7 is cup-shaped, having an annular rim which can sealingly engage the spherical surface of the ball. The elastic insert 7 represented in FIG. 3 is designed concurrently as the lining of the liquid chamber 3. It is sufficient, however, for obtaining the desired sealing effect, to design the elastic insert 7 as a sealing ring.

The liquid chamber 3 as shown in FIG. 1 is arranged eccentrically in the socket cavity so that it is positioned in the actual stress zone of the ball head support of the femoral prosthesis in order to obtain optimal distribution of forces and sealing. The diameter of the liquid chamber 3 depends upon the particular design and size of the artificial hip joint socket and is defined in the representations of FIGS. 2 and 3 by an aperture angle a of 60° seen from the hollow sphere center 8.

What is claimed is:

1. An artificial hip joint socket for receiving and cooperating with a ball head of a femoral prosthetic shaft comprising
   a hollow body having a wall and a spherical inner surface with means defining a recess with a circular opening extending into said wall from said inner surface forming a filled liquid chamber, said recess being positioned eccentrically at the spherical region of the hip joint socket at the stress zone of the femoral head support, said means defining said recess opening including a circular edge at the line of junction with said spherical inner surface defining the sole opening into said liquid chamber, said edge substantially continuously forming a latitudinal seal with said ball head so that an increase of pressure of said ball against said spherical surface allows an increase in hydrostatic pressure in said liquid chamber.

2. A socket according to claim 1 wherein said hollow body is formed from an elastic material, said seal being formed by elastic deformation of said edge.

3. A socket according to claim 1 wherein the diameter of the latitudinal seal forms an aperture angle of about 110° relative to the center of said spherical inner surface.

4. A socket according to claim 1 wherein the diameter of the latitudinal seal forms an aperture angle of about 60° relative to the center of said spherical inner surface.

5. A socket according to claim 1 wherein said hollow body comprises a substantially rigid material and said means defining said recess comprises an annular insert of elastic material, said insert forming said edge, said seal being formed by elastic deformation of said edge.

6. A socket according to claim 5 wherein the diameter of the latitudinal seal forms an aperture angle of about 110° relative to the center of said spherical inner surface.

7. A socket according to claim 6 wherein the diameter of the latitudinal seal forms an aperture angle of about 60° relative to the center of said spherical inner surface.

8. A socket according to claim 1 wherein said hollow body comprises a substantially rigid material and said means defining said recess comprises a generally cup-shaped insert of elastic material forming said edge, said seal being formed by elastic deformation of said edge.

9. A socket according to claim 8 wherein the diameter of the latitudinal seal forms an aperture angle of about 110° relative to the center of said spherical inner surface.

10. A socket according to claim 8 wherein the diameter of the latitudinal seal forms an aperture angle of about 60° relative to the center of said spherical inner surface.

11. An artificial hip joint socket for receiving and cooperating with a ball head of a femoral prosthetic shaft comprising
 a hollow body having a wall and a spherical inner surface for receiving the ball head of the prosthetic shaft such that said ball head and said spherical surface have a common center, said body further including means defining a recess extending into said wall from said inner surface forming a liquid chamber, said recess being positioned at the stress zone of the femoral head support,
 said means defining said recess including a circular edge at the line of junction with said spherical inner surface defining the sole opening into said liquid chamber, said edge forming a permanent latitudinal seal with said ball head when said joint is under load so that an increase of pressure of said ball against said spherical surface allows an increase in hydrostatic pressure in said liquid chamber.

* * * * *